(12) United States Patent
Barnett

(10) Patent No.: US 9,254,323 B2
(45) Date of Patent: *Feb. 9, 2016

(54) METHOD AND PRODUCTS FOR ENHANCING CELLULAR UPTAKE OF DRUG AND DIETARY SUPPLEMENTS

(71) Applicant: CBA Pharma, Inc., Lexington, KY (US)

(72) Inventor: Daryl L. Barnett, Lexington, KY (US)

(73) Assignee: CBA Pharma, Inc., Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/206,739

(22) Filed: Mar. 12, 2014

(65) Prior Publication Data

US 2014/0275157 A1 Sep. 18, 2014

Related U.S. Application Data

(60) Provisional application No. 61/793,028, filed on Mar. 15, 2013.

(51) Int. Cl.
| | | |
|---|---|---|
| *A23L 1/30* | (2006.01) | |
| *A61K 31/4725* | (2006.01) | |
| *A61K 45/06* | (2006.01) | |
| *A61K 31/4745* | (2006.01) | |

(52) U.S. Cl.
CPC . *A61K 45/06* (2013.01); *A23L 1/30* (2013.01); *A61K 31/4745* (2013.01)

(58) Field of Classification Search
CPC ....... A61K 31/4725; A61K 45/06; A23L 1/30
USPC ......................................................... 514/308
See application file for complete search history.

(56) References Cited

U.S. PATENT DOCUMENTS

| | | |
|---|---|---|
| 6,086,915 A | 7/2000 | Zeligs et al. |
| 6,350,476 B1 | 2/2002 | Hou |
| 2014/0275140 A1* | 9/2014 | Barnett .................... 514/279 |

FOREIGN PATENT DOCUMENTS

| | | |
|---|---|---|
| WO | 9218131 | 10/1992 |

OTHER PUBLICATIONS

Li, et al., Paclitaxel/Tetrandrine Coloaded Nanoparticles Effectively Promote the Apoptosis of Gastric Cancer Cells Based on "Oxidation Therapy", Mol. Pharmaceutics, 9, 222-229 (2012).*

* cited by examiner

*Primary Examiner* — Erich A Leeser
(74) *Attorney, Agent, or Firm* — Mitchell Intellectual Property Law, PLLC

(57) ABSTRACT

Enhancing the cellular uptake of a drug or dietary supplement by administering it concurrently with one or more members of the d-tetrandrine family.

20 Claims, No Drawings

METHOD AND PRODUCTS FOR ENHANCING CELLULAR UPTAKE OF DRUG AND DIETARY SUPPLEMENTS

CROSS REFERENCE TO RELATED APPLICATIONS

The present application claims the benefit of U.S. Provisional Patent Application No. 61/793,028, entitled METHOD AND PRODUCTS FOR ENHANCING CELLULAR UPTAKE OF DRUG AND DIETARY SUPPLEMENTS, filed on Mar. 15, 2013, the entire contents of which are incorporated by reference.

FIELD AND BACKGROUND OF THE INVENTION

The present invention relates to the administration of drugs and dietary supplements, including nutraceuticals. The effectiveness of drugs and dietary supplements is in part a function of their uptake by the cells they are intended to affect. Various devices and compounds have been proposed for enhancing cellular uptake, such as:

Gold nanoparticles: Transferrin-mediated gold nanoparticle cellular uptake P H Yang, X Sun, J F Chiu, H Sun, Q Y He—Bioconjugate chemistry; 2005—ACS Publications Cell fixation: Cell-penetrating peptides a reevaluation of the mechanism of cellular uptake J P Richard, K Melikov, E Vives, C Ramos . . . —Journal of Biological . . . , 2003—ASBMB Gold phosphene: Role of lipophilicity in determining cellular uptake and antitumor activity of gold phosphine complexes M J McKeage, S J Berners-Price, P Galettis . . . —Cancer chemotherapy . . . 2000—Springer Polymeric nanoparticles: Effects of particle size and surface coating on cellular uptake of . . . www.ncbi.nlm.nih.gov/pubmed/15585275 by K Y Win—2005—

Cell penetrating peptides: Mechanisms of Cellular Uptake of Cell-Penetrating Peptides www.hindawi.com/journals/jbp/2011/414729/Cached by F Madani—2011

SUMMARY OF THE INVENTION

In the present invention, cellular uptake of drugs and dietary supplements is enhanced by the concurrent administration of particular members of the d-tetrandrine family of drugs. The d-tetrandrine family members have the following structural formula:

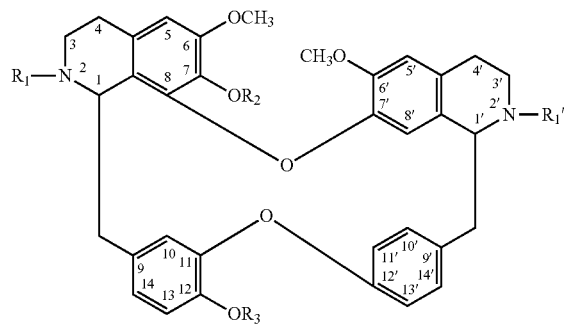

Where $R_1$ and $R_1'$ are the same or different shortchained carbon based ligand including without limitation, $CH_3$, $CO_2CH_3$ or H; and $R_2$ is $CH_3$ or $C_2H_5$; and $R_3$ is $CH_3$ or hydrogen; and where the chemical structure has the "S" isomeric configuration at the C-1' chiral carbon location.

DESCRIPTION OF THE PREFERRED EMBODIMENT

The preferred members of the d-tetrandrine family include the following representative examples, which are not intended to be exhaustive: d-tetrandrine, isotetrandrine, hernandezine, berbamine, pycamine, phaeanthine, obamegine, ethyl fangchinoline and fangchinoline. In all of these examples, $R_1$ and $R_1'$ constitute the methyl group. Variation within the group occurs in that $R_2$ and $R_3$ may constitute either a methyl group or hydrogen, and the isometric configuration of the compounds at the C-1 and C-1' chiral carbon positions is either R (rectus) or S (sinister). The rules for R and S configuration can be found in Morrison and Boyd, "Organic Chemistry," 4th Edition, copyright 1983 by Allyn and Bacon, at pp. 138-141. As noted above, the chiral configuration at C-1' is "S" for members of the d-tetrandrine family. In addition, hernandezine includes a methoxy group at the C-5 position.

The most-preferred member of the claimed tetrandrine family is d-tetrandrine. Methods for extracting and/or purifying d-tetrandrine are disclosed in U.S. Pat. No. 6,218,541 and in Published Patent Application No. 2011/0105755.

The cellular uptake of drugs and dietary supplements varies from product to product and type of cell. The extent to which concurrent administration of a d-tetrandrine family member enhances the extent and rate of such uptake will also vary accordingly. Those drugs and dietary supplements with rapid and more complete rates of uptake may show little or no improvement in cellular uptake through the concurrent use of a d-tetrandrine family member. However, many drugs and dietary supplements with slower and less complete rates of cellular uptake will show improvement with such concurrent use.

The d-tetrandrine family member and the drug or dietary supplement can be formulated together into a single formula, or they can be formulated separately and administered either simultaneously or sufficiently close together that they are both in the target cell area at the same time. The d-tetrandrine family member and the drug or dietary supplement can formulate separately but be sold as part of a "kit." The usage ratio of the d-tetrandrine family member to a drug or dietary supplement will vary from patient to patient and as a function of the principle drug or dietary supplement used, within a range of from about 0.04:1 to about 170:1. A more typical range would be from about 1:1 to 100:1, more preferably from 25:75 to 75:25.

It is believed that the optimum dosage procedure would be to administer the d-tetrandrine family member in oral doses of from about 50 to about 1000 mg per square per day, more preferably 250-700, and most preferably about 500, (probably in two to four doses per day), while administering the drug or dietary supplement simultaneously or on the same day. The dosage level for the d-tetrandrine family member will vary from case to case, based on the patient and on the drug or dietary supplement used. The drug or dietary supplement is administered at usual dosage levels (possibly somewhat less in view of the effect of the tetrandrine family member on cellular uptake) once or more during the course of the d-tetrandrine family member dosing.

It is also believed that the dosage procedure could spread out the administration of the d-tetrandrine family member in oral doses of from about 50 to about 1000 mg per square meter per day, more preferably 250-700, and most preferably about 500, (probably in two to four doses per day) over a period of from about 4 to about 14 days. The dosage level for the d-tetrandrine family member will vary from case to case, based on the patient and on the drug or dietary supplement used. The drug or dietary supplement is then administered at usual dosage levels (possibly somewhat less in view of the potentiation effect of the d-tetrandrine family member) once or more during the course of the d-tetrandrine family member dosing. For example, during a four day period of d-tetrandrine administration, the drug or dietary supplement would be administered on the beginning of the third day. Over a 14 day period, the drug or dietary supplement might be administered on day 5 and day 10, or on days 4, 8 and 12. Such administration is considered concurrent for purposes of this invention.

The d-tetrandrine family bisbenzylisoquniolines have two nitrogen locations and hence can exist in the free base form or as a mono or di-acid salt. Because of the enhanced solubility of the salt form of pharmaceutical ingredients, the salt forms are used in formulating pharmaceutical composition. The active ingredient thus solubilizes more quickly and enters the bloodstream faster. The free base form is not soluble in water. However, it has recently been surprisingly found by a coworker that the free base formulations of d-tetrandrine family members are absorbed into the bloodstream substantially as rapidly as formulations of the di-acid salt members of the family. Accordingly, we propose to use either the free base or the di-acid salt of the d-tetrandrine family member in our formulations.

The preferred formulations comprise a member of the d-tetrandrine family combined with a suitable pharmaceutical carrier. The pharmaceutical carrier can be a liquid or a solid composition. A liquid carrier will preferably comprise water, possibly with additional ingredients such as 0.25% carboxymethylcellulose. The solid carrier or diluent used may be pregelatinized starch, microcrystalline cellulose or the like. It may also be formulated with other ingredients, such as colloidal silicone dioxide, sodium lauryl sulfate and magnesium stearate.

A 200 mg capsule, tablet or liquid dosage formulation is most preferred. The most preferred dose of about 500 mg/square meter/day is roughly 1000 mg per day for a 190 pound patient six feet tall. Such a patient can fulfill the dosage requirements by taking five capsules during the course of the day, for example three in the morning and two in the evening, or one at a time spaced out over the day. A smaller person weighing 125 pounds at a height of five feet six inches would require four 200 mg capsules during the course of the day.

Of course, it is understood that the forgoing are preferred embodiments of the invention, and that variations can be employed without departing from the spirit of the invention as set forth in the appended claims, interpreted in accordance with the principles of patent law.

The invention claimed is:

1. A method of enhancing the cellular uptake of drugs and dietary supplements comprising:

the concurrent administration of a drug or dietary supplement and a member of the d-tetrandrine family of drugs having the following structural formula:

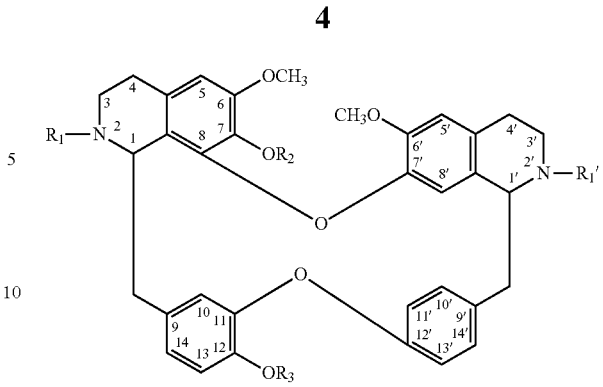

where $R_1$ and $R_1'$ are the same or different short chained carbon based ligand including without limitation, $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location.

2. The method of claim 1 wherein said member of the d-tetrandrine family is selected from the group consisting of: d-tetrandrine, isoretrandrine, hernandezine, berbamine, pyenamine, phaeanthine, obamegine, ethyl fangchinoline and fangchinoline.

3. The method of claim 1 wherein said member of the d-tetrandrine family is d-tetrandrine.

4. The method of claim 3 in which the d-tetrandrine family member is used in conjunction with a drug.

5. The method of claim 4 in which the d-tetrandrine family member and the drug are formulated together into a single formula.

6. The method of claim 1 in which the d-tetrandrine family member is used in conjunction with a drug.

7. The method of claim 1 in which the drug or dietary supplement normally has a rate of cellular uptake which is at the slower and/or less complete one third portion of on a scale of cellular uptake for various drugs and dietary supplement.

8. The method of claim 1 in which the d-tetrandrine family member and the drug or dietary supplement are formulated together into a single formula.

9. The method of claim 1 in which the d-tetrandrine family member and the drug or dietary supplement are formulated separately and administered either simultaneously or sufficiently close together that the MRSA is exposed to both simultaneously.

10. The method of claim 1 in which the d-tetrandrine family member and drug or dietary supplement are administered in a usage ratio of d-tetrandrine family member to drug or supplement, within a range of from about 0.04 to about 170.

11. The method of claim 1 in which the d-tetrandrine family member and drug or dietary supplement are administered in a usage ratio of d-tetrandrine family member to drug or dietary supplement, within a range of from about 1 to 100.

12. The method of claim 1 in which the d-tetrandrine family member and drug or dietary supplement are administered in a usage ratio of d-tetrandrine family member to drug or dietary supplement, within a range of from about 25:75 to 75:25.

13. A method of enhancing the cellular uptake of dietary supplements comprising:

the concurrent administration of a dietary supplement and a member of the d-tetrandrine family of drugs having the following structural formula:

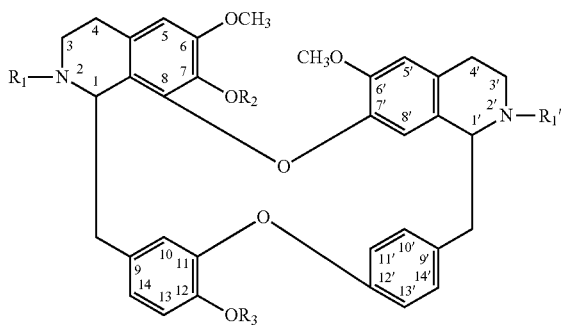

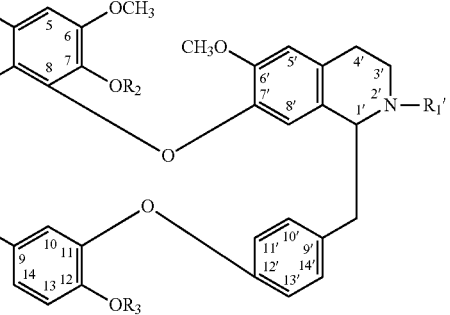

where $R_1$ and $R_1'$ are the same or different short chained carbon based ligand including without limitation, $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location.

14. The method of claim 13 wherein said member of the d-tetrandrine family is d-tetrandrine.

15. The method of claim 14 in which the d-tetrandrine family member and the dietary supplement are formulated together into a single formula.

16. A method of enhancing the cellular uptake of drugs and dietary supplements comprising:

the concurrent administration of a drug or dietary supplement and a member of the d-tetrandrine family of drugs having the following structural formula:

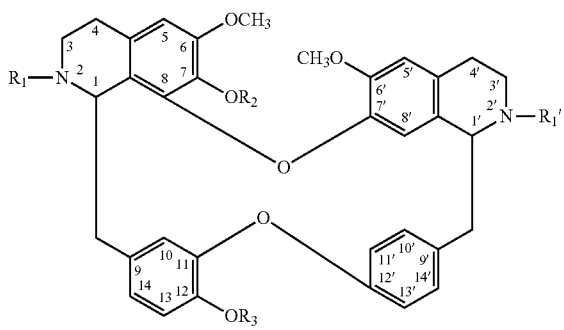

where $R_1$ and $R_1'$ are the same or different short chained carbon based ligand including without limitation, $CH_2$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location, said d-tetrandrine family member being administered in oral doses of from about 50 to about 1000 mg per square meter per day over a period of from about 4 to about 14 days, and the drug or dietary supplement is then administered at usual dosage levels once or more during said 4 to 14 days.

17. A method of enhancing the cellular uptake of drugs and dietary supplements comprising:

the administration of a formulation of a drug or dietary supplement and a member of the d-tetrandrine family of drugs having the following structural formula:

where $R_1$ and $R_1'$ are the same or different short chained carbon based ligand including without limitation, $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location, said formulation being administered such that said d-tetrandrine family member is administered in oral doses of from about 250-700 mg per square meter per day over said period of from about 4 to about 14 days.

18. A method of enhancing the cellular uptake of drugs and dietary supplements comprising:

the administration of a formulation of a drug or dietary supplement and a member of the d-tetrandrine family of drugs having the following structural formula:

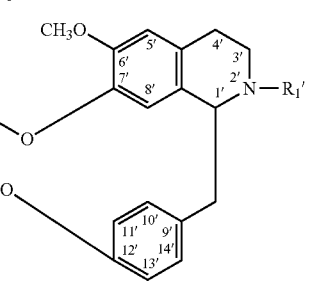

where $R_1$ and $R_1'$ are the same or different short chained carbon based ligand including without limitation, $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location, said formulation being administered such that said d-tetrandrine family member is administered in oral doses of about 500 mg per square meter per day over said period of from about 4 to about 14 days, in two to four doses per day.

19. A dietary supplement composition providing an enhanced level of cellular uptake of the dietary supplement ingredient, comprising a dietary supplement combined with a member of the d-tetrandrine family having the following structural formula:

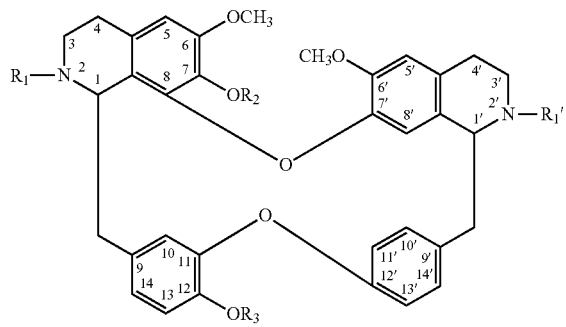

where $R_1$ and $R_1'$ are the same or different short chained carbon based ligand including without limitation, $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location.

20. A dietary supplement kit providing an enhanced level of cellular uptake of the dietary supplement ingredient, including a dietary supplement, and a formulation comprising a member of the d-tetrandrine family having the following structural formula:

where $R_1$ and $R_1'$ are the same or different short chained carbon based ligand including without limitation, $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location.

\* \* \* \* \*